(12) United States Patent
Shao et al.

(10) Patent No.: US 10,748,291 B2
(45) Date of Patent: *Aug. 18, 2020

(54) LIVER BOUNDARY IDENTIFICATION METHOD AND SYSTEM

(71) Applicant: WUXI HISKY MEDICAL TECHNOLOGIES CO., LTD., Wuxi (CN)

(72) Inventors: Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,529

(22) Filed: May 20, 2019

(65) Prior Publication Data

US 2019/0272644 A1 Sep. 5, 2019

Related U.S. Application Data

(63) Continuation of application No. 15/487,032, filed on Apr. 13, 2017, now Pat. No. 10,354,390, which is a (Continued)

(30) Foreign Application Priority Data

Oct. 21, 2014 (CN) .......................... 2014 1 0564295

(51) Int. Cl.
*G06T 7/13* (2017.01)
*G06K 9/00* (2006.01)
(Continued)

(52) U.S. Cl.
CPC .............. *G06T 7/13* (2017.01); *A61B 8/0858* (2013.01); *A61B 8/5223* (2013.01);
(Continued)

(58) Field of Classification Search
CPC ... G06T 7/13; G06T 7/11; G06T 2207/10081; G06T 2207/10088; G06T 2207/10132; G06T 2207/30056
See application file for complete search history.

(56) References Cited

U.S. PATENT DOCUMENTS

| 6,067,371 A | 5/2000 | Gouge et al. |
| 6,370,480 B1 | 4/2002 | Gupta et al. |

(Continued)

FOREIGN PATENT DOCUMENTS

| CN | 101261732 A | 9/2008 |
| CN | 101425186 A | 5/2009 |

(Continued)

OTHER PUBLICATIONS

Afifi, Ahmed et al, "Shape-Based Liver Segmentation Without Prior Statistical Models" Abdomen and Thoracic Imaging—an Engineering & Clinical Perspective by Ayman El-Baz et al.; Springer New York Heidelberg Dordrecht London; ISBN: 978-1-4614-8497-4; (Jan. 2014); pp. 279-315.

(Continued)

*Primary Examiner* — Kim Y Vu
*Assistant Examiner* — Molly Delaney
(74) *Attorney, Agent, or Firm* — J.C. Patents

(57) ABSTRACT

The present disclosure relates to the technical field of medical image processing and, in particular, to a liver boundary identification method and a system. The method includes: obtaining liver tissue information of a liver tissue to be identified; identifying a liver tissue boundary in the liver tissue information according to a feature of the liver tissue corresponding to the liver tissue information and a feature of the liver tissue boundary corresponding to the liver tissue information using an image processing technology or a signal processing technology; and outputting posi- (Continued)

tion information of the identified liver tissue boundary. By using the disclosed method, the liver tissue boundary can be identified automatically, the efficiency of identifying the liver boundary can be improved, and automatic positioning of the liver boundary can thus be achieved.

19 Claims, 6 Drawing Sheets

Related U.S. Application Data continuation of application No. PCT/CN2015/081838, filed on Aug. 10, 2015.

(51) Int. Cl.
*G06T 7/136* (2017.01)
*A61B 8/08* (2006.01)
*G06T 7/12* (2017.01)
*G06T 7/187* (2017.01)
*G06T 7/00* (2017.01)
*G06T 7/11* (2017.01)
*G06T 7/10* (2017.01)

(52) U.S. Cl.
CPC ........ *G06K 9/00523* (2013.01); *G06T 7/0012* (2013.01); *G06T 7/10* (2017.01); *G06T 7/11* (2017.01); *G06T 7/12* (2017.01); *G06T 7/136* (2017.01); *G06T 7/187* (2017.01); *G06T 2207/10081* (2013.01); *G06T 2207/10088* (2013.01); *G06T 2207/10132* (2013.01); *G06T 2207/20076* (2013.01); *G06T 2207/30008* (2013.01); *G06T 2207/30012* (2013.01); *G06T 2207/30056* (2013.01)

(56) References Cited

U.S. PATENT DOCUMENTS

| | | | |
|---|---|---|---|
| 7,519,209 | B2 | 4/2009 | Dawant |
| 7,702,153 | B2 | 4/2010 | Hong |
| 10,354,390 | B2 * | 7/2019 | Shao .......................... G06T 7/13 |
| 2002/0070970 | A1 | 6/2002 | Wood et al. |
| 2006/0013482 | A1 | 1/2006 | Dawant et al. |
| 2006/0064396 | A1 * | 3/2006 | Wei ........................ A61B 6/463 |
| 2008/0123927 | A1 * | 5/2008 | Miga ........................ G06T 7/344 |
| | | | 382/131 |
| 2010/0081931 | A1 | 4/2010 | Destrempes et al. |
| 2011/0172533 | A1 * | 7/2011 | Yao .......................... A61B 8/08 |
| | | | 600/443 |
| 2012/0070055 | A1 * | 3/2012 | Liu ........................ G06T 7/0016 |
| | | | 382/131 |
| 2013/0178740 | A1 | 7/2013 | Han |
| 2014/0193053 | A1 | 7/2014 | Kadoury et al. |
| 2015/0025372 | A1 * | 1/2015 | Ghosh .................... G06T 7/0014 |
| | | | 600/431 |
| 2015/0148658 | A1 * | 5/2015 | Smith .................. A61B 5/4244 |
| | | | 600/410 |

FOREIGN PATENT DOCUMENTS

| | | |
|---|---|---|
| CN | 102125444 A | 7/2011 |
| CN | 102956035 A | 3/2013 |
| CN | 102125444 B | 2/2014 |
| CN | 103914710 A | 7/2014 |
| CN | 104408398 A | 3/2015 |
| JP | 2002-233527 A | 8/2002 |
| JP | 2003-061964 A | 3/2003 |
| JP | 2006-095002 A | 4/2006 |
| JP | 2006-296495 A | 11/2006 |
| JP | 5542454 B2 | 5/2014 |
| KR | 10-1913977 B1 | 10/2018 |
| RU | 2407426 C1 | 12/2010 |
| WO | 2007135884 A1 | 11/2007 |
| WO | 2007142255 A1 | 12/2007 |
| WO | 2009060751 A1 | 5/2009 |
| WO | 2011083789 A1 | 7/2011 |
| WO | 2014083480 A1 | 6/2014 |
| WO | 2014132209 A1 | 9/2014 |

OTHER PUBLICATIONS

Bakhmutova E.E., "Is it Possible to Diagnosed Hypervascular Mass with Homogeneous Enchancement at Arterial Phase by one Tomography Method (CT, MR)" Annuals of Surgical Hepatology, No. 3, (2016), pp. 50-58.

Chen M.F. et al., "Segmentation of liver in ultrasonic images applying local optimal threshold method" the Imaging Science Journal; vol. 61, Issue 7; (2013); pp. 579-591.

Cui, Zhenchao et al., "Fast marching over the 2D Gabor magnitude domain for tongue body segmentation" Eurasip Journal on Advances in Signal Process, (2013), vol. 190.

Destrempes, Francois et al., "Review of Envelope Statistics Models for Quantitative Ultrasound Imaging and Tissue Characterization" chapter 10 of Quantitative Ultrasound in Soft Tissues; (Sep. 2013); pp. 219-277.

Feng, Xuetao et al., "Learning based ensemble segmentation of anatomical structures in liver ultrasound image" Conference Paper in Proceedings of SPIE—the International Society for Optical Engineering; (Mar. 2013); vol. 8669 Medical Imaging 2013: Image Processing.

Foruzan, Amir H. et al., "A knowledge-based technique for liver segmentation in CT data" Computerized Medical Imaging and Graphics; vol. 33, Issue 8; (Dec. 2009); pp. 567-587.

Li, Yuanzhong et al., "A Machine Learning Approach for Locating Boundaries of Liver Tumors in CT Images" Proceeding of the 18th International Conferences of Pattern Recognition (ICPR'06).

Mamou, Jonathan et al., "Quantitative Ultrasound in Soft Tissues" Springer New York Heidelberg Dordrecht London; ISBN: 978-94-007-6951-9; (Jan. 2013).

Milko, Sergiy et al., "Segmentation of the liver ultrasound: a dynamic texture approach" International Journal of Computer Assisted Radiology and Surgery; vol. 3; (Jun. 2008); pp. 143-150.

Naohisa, Kamiyama et al., "Investigation on Method of extracting tiny structure by using similarity of speckle patterns in ultrasonic image" Japanese Acoustics Society Lectures, (Oct. 2001), pp. 1271-1272.

Parker, Kevin J. et al., "Absorption and Attenuation in Soft Tissues: I-Calibration and Error Analyses" IEEE Transactions on Ultrasonics Ferroelectrics and Frequency Control, vol. 35, No. 2, (Mar. 1988), pp. 242-252.

Yamaguchi, Tadashi et al., "The Quantitative Ultrasound Diagnosis of Liver Fibrosis Using Statistical Analysis of the Echo Envelope" chapter 11 of Springer New York Heidelberg Dordrecht London; ISBN: 978-94-007-6951-9; (Jan. 2013); pp. 275-288.

Yoshida, Hiroyuki et al., "Segmentation of Liver Tumors in Ultrasound Images based on Scale-Space Analysis of the Continuous Wavelet Transform" Proceedings of the IEEE Ultrasonics Symposium; vol. 2; (Feb. 1998); pp. 1713-1716.

The Australian Examination Report No. 1 for standard patent application of corresponding Australian application No. 2015335555, dated Nov. 10, 2017.

The Australian Examination Report No. 2 for standard patent application of corresponding Australia patent application No. 2015335555, dated Feb. 1, 2018.

The Australian Examination Report No. 1 for your standard patent application of corresponding Australian application No. 2018206806, dated Apr. 8, 2019.

The Australian Examination Report No. 1 for your standard patent application of corresponding Australian application No. 2018206807, dated Apr. 8, 2019.

The Chinese First Examination Report of corresponding Chinese patent application No. 201410564295.5, dated Mar. 20, 2017.

The Chinese Third Examination Report of corresponding Chinese patent application No. 201410564295.5, dated Jan. 17, 2018.

(56) References Cited

OTHER PUBLICATIONS

The supplementary European Search Report of corresponding European patent application No. 15853412.3-1207/3211561, dated May 29, 2018.
The extended European Search Report of corresponding European patent application No. 15853412.3-1207/3211561, dated Sep. 10, 2018.
The International Search Report of corresponding international PCT application No. PCT/CN2015/081838, dated Sep. 14, 2015.
The Japanese Examination Report of corresponding Japanese application No. 2017-512989, dated Apr. 17, 2019.
The Korean Examination Report of corresponding Korea patent application No. 10-2017-7006751, dated Sep. 28, 2018.
The Korean Examination Report of corresponding Korea patent application No. 10-2017-7006751, dated Feb. 2, 2018.
The Russian Examination Report of corresponding Russian Federation patent application No. 2017117302/14 (029954), dated Apr. 19, 2018.
The Russian Examination Report of corresponding Russian Federation patent application No. 2017117302/14 (029954), dated Sep. 13, 2018.
D1: "Liver segmentation from computed tomography scans", Artificial Intelligence in Medicine, (2009) 45, 185-196.
D2: "Implicit Active Shape Model Employing Boundary Classifier", 978-1-4244-2175-6/08/ 2008IEEE.
D3: "2D segmentation of computed tomography images based on integrated neighborhood", No. 2 2008.
First Office Action of the parallel RU application.
"A Machine Learning Approach for Locating Boundaries of Liver Tumors in CT Images", Proceedings of the 18th International Conference on Pattern Recognition (ICPR'06) 0-7695-2521-0/06, 2006 IEEE.
"Quantitative_Ultrasound_in_Soft_Tissues_Abstract", Published 2003.
"Segmentation of Liver Tumors in Ultrasound Images based on Scale-Space Analysis of the Continuous Wavelet Transform", 1998 IEEE Ultrasonics Symposium, p. 1713-1716.
First Office Action of the parallel BR application.

* cited by examiner

US 10,748,291 B2

LIVER BOUNDARY IDENTIFICATION METHOD AND SYSTEM

CROSS-REFERENCE TO RELATED APPLICATIONS

This application is a continuation of U.S. patent application Ser. No. 15/487,032, filed on Apr. 13, 2017, which is a continuation of International Application No. PCT/CN2015/081838, filed on Aug. 10, 2015. The International Application claims priority to Chinese Patent Application No. 201410564295.5, filed on Oct. 21, 2014. All of the aforementioned patent applications are hereby incorporated by reference in their entireties.

TECHNICAL FIELD

The present disclosure relates to the technical field of medical image processing and, in particular, to a liver boundary identification method and a system.

BACKGROUND

Many clinical applications require identifying a liver tissue boundary from conventional medical imaging including ultrasonic imaging, magnetic resonance imaging (MRI), computed tomography (CT) and so on, so as to locate a liver examination region, such as for liver elasticity examination and liver color Doppler ultrasonography etc.

At present, the liver tissue boundary is mostly identified manually. However, selecting the liver boundary manually according to liver tissue information requires the operator to be highly familiar with the liver tissue structure and image information so that the liver tissue boundary can be selected accurately, which is very demanding for the operator. Meanwhile, the relatively long time it takes to manually conduct the identification in the identification process can lead to low efficiency in identifying the liver boundary.

SUMMARY

An objective of the present disclosure lies in proposing a liver boundary identification method and a system to improve the efficiency of liver boundary identification.

On an aspect, the present disclosure provides a liver boundary identification method, including:
obtaining liver tissue information of a liver tissue to be identified;
identifying a liver tissue boundary in the liver tissue information according to a feature of the liver tissue corresponding to the liver tissue information and a feature of the liver tissue boundary corresponding to the liver tissue information using an image processing technology or a signal processing technology; and
outputting position information of the identified liver tissue boundary.

On another aspect, the present disclosure provides a liver boundary identification system, including an information obtaining device, a liver boundary identifying device, and a liver boundary displaying device, where the information obtaining device is configured to obtain liver tissue information of a liver tissue to be identified; the liver boundary identifying device is configured to identify a liver tissue boundary in the liver tissue information according to a feature of the liver tissue corresponding to the liver tissue information and a feature of the liver tissue boundary corresponding to the liver tissue information using an image processing technology or a signal processing technology; and the liver boundary displaying device is configured to output position information of the identified liver tissue boundary.

The liver boundary identification method and the system provided in embodiments of the present disclosure can identify the liver boundary region efficiently. According to the liver boundary identification method provided in embodiments of the present disclosure, the liver tissue information of the liver tissue to be identified is obtained, and then the image processing technology or signal processing technology is employed to identify the liver tissue boundary according to signal features of the liver tissue and its boundary. By using the disclosed method, the liver tissue boundary can be identified automatically, and the efficiency of identifying the liver tissue boundary can be improved.

BRIEF DESCRIPTION OF DRAWINGS

The figures described herein are intended to provide further understanding about embodiments of the present disclosure, and constitute a part of, rather than a limitation on, the embodiments of the present disclosure. In the figures.

DETAILED DESCRIPTION

Now, embodiments of the present disclosure will be more fully and comprehensively described in combination with the accompanying drawings and particular embodiments. It will be appreciated that the particular embodiments described herein are merely used for explaining, rather than limiting, embodiments of the present disclosure. In addition, it should be further noted that in order to facilitate the description, the drawings only depict portions relevant to the embodiments of the present disclosure, rather than the whole content.

First Embodiment

Figure 1:
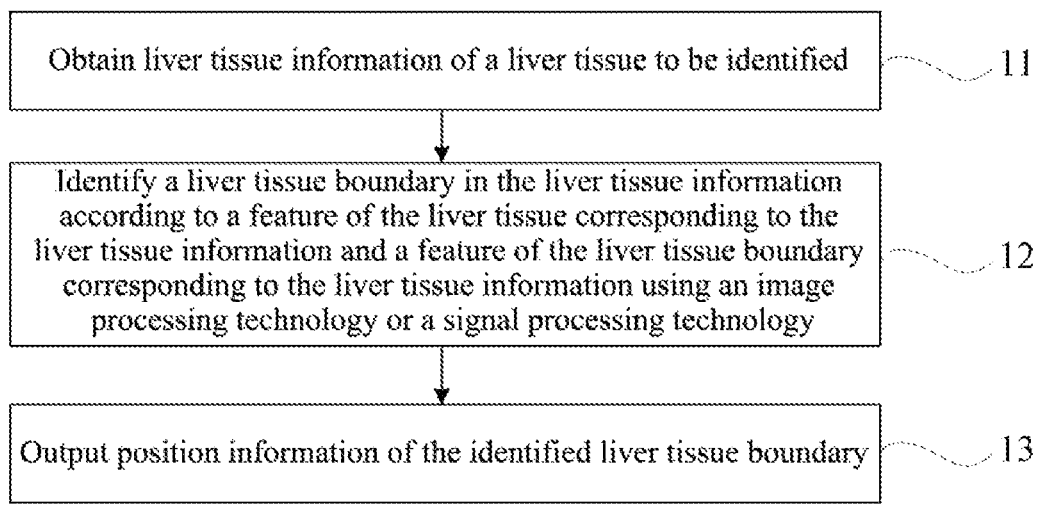
FIG. 1 is a flowchart implementing a liver boundary identification method provided in a first embodiment of the present disclosure.

FIG. 1 is a flowchart implementing a liver boundary identification method provided in a first embodiment of the present disclosure. The method can be performed by a liver boundary identification system. As depicted in FIG. 1, the implementation process includes:

Step 11: obtain liver tissue information of a liver tissue to be identified.

The liver tissue information may be an A-type ultrasonic signal of the liver tissue, an M-type ultrasonic signal of the liver tissue, a B-type ultrasonic image of the liver tissue, a CT image of the liver tissue, or an MRI image of the liver tissue.

According to the liver tissue information, the type of the liver tissue information can be obtained. That is, the type of the liver tissue information may be an ultrasonic signal, e.g. an A-type ultrasonic signal of the liver tissue and an M-type ultrasonic signal of the liver tissue, or a two-dimensional ultrasonic image, e.g. a B-type ultrasonic image of the liver tissue, or a three-dimensional image, e.g. a CT image of the liver tissue and an MRI image of the liver tissue.

Step 12: identify a liver tissue boundary in the liver tissue information according to a feature of the liver tissue corresponding to the liver tissue information and a feature of the liver tissue boundary corresponding to the liver tissue information using an image processing technology or a signal processing technology.

If the liver tissue information is an ultrasonic signal of the liver tissue, use the signal processing technology to identify the liver tissue boundary based on the features of the liver tissue and the liver tissue boundary corresponding to the ultrasonic signal of the liver tissue; if the liver tissue information is a two-dimensional ultrasonic image or a three-dimensional image, use the image processing technology to identify the liver tissue boundary based on the features of the liver tissue and the liver tissue boundary corresponding to the two-dimensional ultrasonic image or three-dimensional ultrasonic image of the liver tissue.

When the liver tissue information is a one-dimensional ultrasonic signal of the liver tissue, a two-dimensional ultrasonic image of the liver tissue or a three-dimensional ultrasonic image of the liver tissue, identifying the liver tissue boundary in the liver tissue information according to the feature of the liver tissue corresponding to the liver tissue information and the feature of the liver tissue boundary corresponding to the liver tissue information using the image processing technology or the signal processing technology may particularly include: partitioning the liver tissue information into a plurality of detection sub-regions; calculating a feature value of the liver tissue information in each detection sub-region; and determining the liver tissue boundary according to the feature values of the liver tissue information in the detection sub-regions.

Step 13: output position information of the identified liver tissue boundary.

Outputting position information of the identified liver tissue boundary may include: outputting a coordinate position of the identified liver tissue boundary; and/or displaying an image of the identified liver tissue boundary. That is, only the coordinate position of the identified liver tissue boundary may be outputted, or only the image of the identified liver tissue boundary may be displayed, or, not only may the coordinate position of the identified liver tissue boundary be outputted, but the image of the identified liver tissue boundary may also be displayed, when outputting the position information of the identified liver tissue boundary.

According to the liver tissue boundary identification method provided in the first embodiment of the present disclosure, the liver tissue boundary can be identified automatically and efficiently according to features of the liver tissue and the liver tissue boundary corresponding to the liver tissue information, where the liver tissue information may be an A-type ultrasonic signal that reflects one-dimensional structural information of the liver tissue or an M-type ultrasonic signal that reflects one-dimensional structural dynamic information of the tissue, or a B-type ultrasonic image that reflects a two-dimensional structure of the liver tissue, or a CT or MRI image that reflects a three-dimensional structure of the liver tissue.

Second Embodiment

Figure 2:
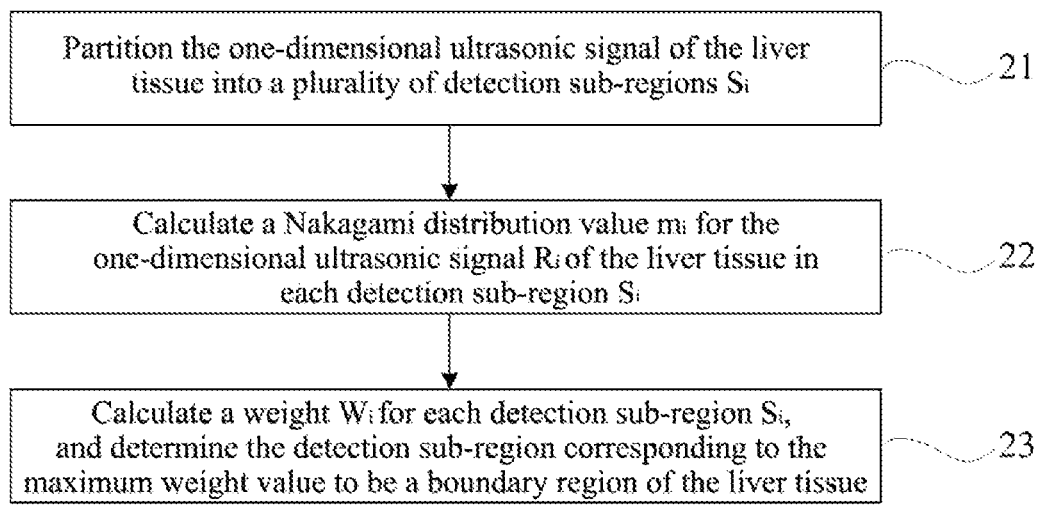
FIG. 2 is a flowchart implementing a liver boundary identification method provided in a second embodiment of the present disclosure.
Figure 3:
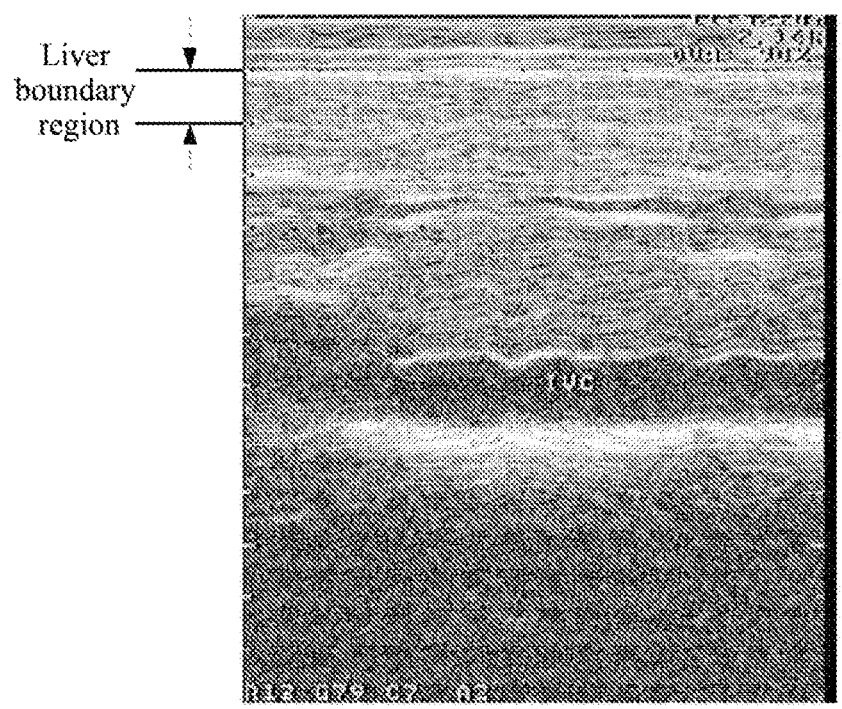
FIG. 3 is a schematic view illustrating an effect of boundary identification based on an M-type ultrasonic signal of a liver tissue in the second embodiment of the present disclosure.

The second embodiment is a particular optimization directed towards the Step 12 in the first embodiment of the present disclosure. The method is applicable to a one-dimensional ultrasonic signal of the liver tissue. FIG. 2 is a flowchart implementing a liver boundary identification method provided in a second embodiment of the present disclosure, and FIG. 3 is a schematic view illustrating an effect of boundary identification based on an M-type ultrasonic signal of the liver tissue in the second embodiment of the present disclosure. Combined with FIGS. 2 and 3, the method includes:

Step 21: partition the one-dimensional ultrasonic signal of the liver tissue into a plurality of detection sub-regions $S_i$.

The one-dimensional ultrasonic signal of the liver tissue may be an A-type ultrasonic signal of the liver tissue or an M-type ultrasonic signal of the liver tissue. Assuming that one ultrasonic signal contains n sampling points and corresponding scanning depth of the ultrasonic signal of the liver tissue is d (in mm), it can be known that each 1 mm depth contains n/d points. The n sampling points are partitioned into multiple detection sub-regions $S_i$, with the detection sub-region $S_i$ corresponding to the scanning depth of $d_i$, where i is an integer, the scanning depth $d_i$ may be an average value of depth or an end value of depth of the detection sub-region $S_i$, and the following will be based on the case of end value.

For instance, n sampling points are partitioned into multiple detection sub-regions $S_i$ with spacing z. The information about the very bottom of an image produced from ultrasonic imaging (which corresponds to the deepest portion of the scanning depth) may be ignored because the very bottom of the image typically does not contain any detection target. In this case, i=1, 2, . . . , [d/z]−1, where z is the section length of a detection sub-region (in mm), and [ ] indicates rounding up to an integer. In this case, each segment of the detection sub-region contains [zn/d] sampling points, respectively. For example, when the scanning depth d of the ultrasonic signal is 20 mm and the spacing z is 3 mm, n sampling points are partitioned into [d/z]−1=6 detection sub-regions $S_1$~$S_6$, where $S_1$ corresponds to the section of 0~3 mm, $S_2$ corresponds to the section of 3~6 mm, . . . , $S_6$ corresponds to the section of 15~18 mm, and the very bottom of the image (which corresponds to the section of 18~20 mm) is ignored because it typically does not contain any testing target.

Step 22: calculate a Nakagami distribution value $m_i$ for the one-dimensional ultrasonic signal $R_i$ of the liver tissue in each detection sub-region $S_i$.

The Nakagami statistic model is a type of ultrasonic tissue characterization technology. Particularly, the Nakagami distribution value $m_i$ is calculated for the ultrasonic signal $R_i$ corresponding to the image of the liver tissue in each detection sub-region $S_i$ according to the following formula:

$$m_i = \frac{[E(R_i^2)]^2}{E[R_i^2 - E(R_i^2)]^2}$$

where the probability density function of the Nakagami distribution is:

$$f(r) = \frac{2m^m r^{2m-1}}{\Gamma(m)\Omega^m} \exp\left(-\frac{m}{\Omega}r^2\right)U(r)$$

where E(.) is a mean value function, $\Gamma$(.) indicates a gamma function, $\Omega = E(r^2)$, U(.) indicates a unit step function, m is the Nakagami distribution value, r is a dependent variable of a probability distribution function f(r), r≥0, m≥0; and for each detection sub-region $S_i$, $m_i$ is the m value in the region $S_i$, and $R_i$ is an envelope value of the ultrasonic signal.

When the m value falls in the range of (0, 1), the ultrasonic signal of liver tissue follows pre-Rayleigh distribution. When the m value equals to 1, the ultrasonic echo-signal follows Rayleigh distribution. When the m value is larger than 1, the ultrasonic echo-signal follows post-Rayleigh distribution.

Step 23: calculate a weight $W_i$ for each detection sub-region $S_i$ according to the following formula, and determine the detection sub-region corresponding to the maximum weight value to be a boundary region of the liver tissue:

$$W_i = \frac{100 * m_i}{\sqrt{d_i}}$$

where $d_i$ is the scanning depth corresponding to the detection sub-region $S_i$, and may also be an average value of depth or an end value of depth of the detection sub-region $S_i$. The weights $W_i$ of respective detection sub-regions are traversed through to pick out the detection sub-region corresponding to the maximum weight value to be a boundary region of the liver tissue, thus accomplishing automatic positioning of the liver tissue boundary.

The liver boundary identification method provided in the second embodiment of the present disclosure is capable of realizing real-time automatic positioning of the liver tissue boundary via A-type or M-type ultrasonic signals of the liver tissue. Additionally, this algorithm has a low complexity level, which can offer higher efficiency in identifying the liver tissue boundary, thereby enabling real-time automatic positioning of the liver tissue boundary.

Third Embodiment

Figure 4:
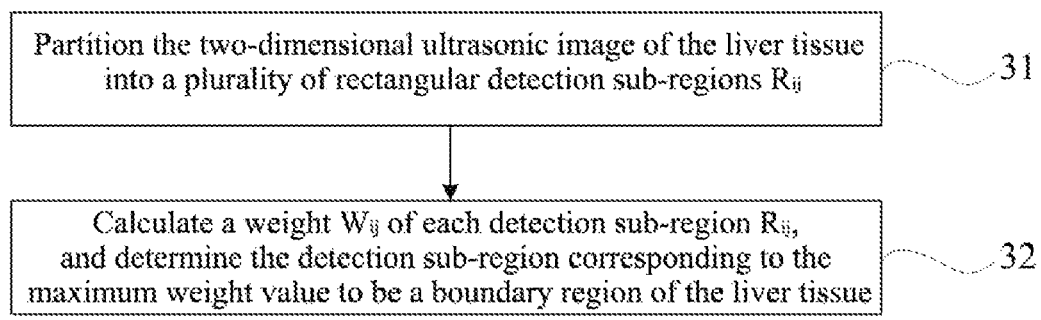
FIG. 4 is a flowchart implementing a liver boundary identification method provided in a third embodiment of the present disclosure.
Figure 5:
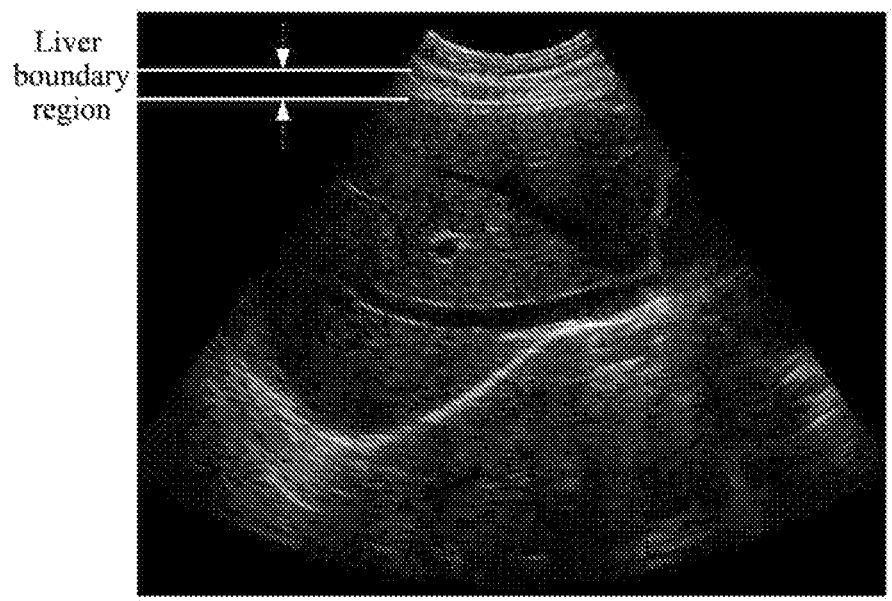
FIG. 5 is a schematic view illustrating an effect of boundary identification based on a B-type ultrasonic image of a liver tissue in the third embodiment of the present disclosure.

The third embodiment is a particular optimization directed towards the Step 12 in the first embodiment of the present disclosure The method is applicable to a two-dimensional ultrasonic signal of the liver tissue. FIG. 4 is a flowchart implementing a liver boundary identification method provided in a third embodiment of the present disclosure, and FIG. 5 is a schematic view illustrating an effect of boundary identification based on a B-type ultrasonic image of the liver tissue in the third embodiment of the present disclosure. Combined with FIGS. 4 and 5, the method includes:

Step 31: partition the two-dimensional ultrasonic image of the liver tissue into a plurality of rectangular detection sub-regions $R_{ij}$, where i and j are natural numbers that indicate the row index and column index of respective detection sub-region, respectively.

The two-dimensional ultrasonic image of the liver tissue may be a B-type ultrasonic image of liver tissue. Assuming that a B-type ultrasonic image has a dimension of w*h, where w is the width of the two-dimensional ultrasonic image of the liver tissue, h is the height of the two-dimensional ultrasonic image of the liver tissue (both w and h are measured by pixel), and the corresponding scanning depth is d (in mm), it can be known that each 1 mm depth along a scanning line in the depth direction contains h/d pixel points. The B-type ultrasonic image of dimension w*h is partitioned into a plurality of rectangular detection sub-regions $R_{ij}$.

For example, the B-type ultrasonic image of dimension w*h is partitioned into multiple square detection sub-regions $R_{ij}$ with side length z. Similar to the first embodiment, the information about the very bottom of the image produced from ultrasonic imaging (which corresponds to the deepest portion of the scanning depth) and the edges thereof along the width direction may be ignored because the very bottom and the edges typically do not contain any testing target, where i=1, 2, . . . , $$\left[\frac{d}{z}\right] - 1,$$

j=1, 2, . . . , $$\left[\frac{wd}{hz}\right] - 1,$$

z is the length of a side of a square detection sub-region (in mm), and [ ] indicates rounding up to an integer. In this case, the width and height of each square detection sub-region $R_{ij}$ are both [zh/d] pixels.

Step 32: calculate a weight $W_{ij}$ of each detection sub-region $R_{ij}$, and determine the detection sub-region corresponding to the maximum weight value to be a boundary region of the liver tissue. In order to reduce the amount of calculation, only weights of half of the detection sub-regions can be calculated. For instance, the two-dimensional ultrasonic image may be split into two portions along a center line, and only the weights $W_{kj}$ (k=$i_{max}$/2) of the detection sub-regions $R_{kj}$ in the upper half of the two-dimensional ultrasonic image are calculated to find out the boundary sub-region above the center line. The complete boundary region can then be obtained by extending the boundary sub-region along the width direction (i.e. lateral direction). In this case, the weight $W_{kj}$ can be calculated according to the following formula:

$$W_{kj} = \frac{M_{kj}}{SD_{kj} * \sqrt{d_{kj}}}$$

where $M_{kj}$ is an average gray value of the two-dimensional ultrasonic image of the liver tissue in the detection sub-region $R_{kj}$, $SD_{kj}$ is standard deviation of grayscale of the two-dimensional ultrasonic image of the liver tissue in the detection sub-region $R_{kj}$, and $d_{kj}$ is scanning depth corresponding to the detection sub-region $R_{kj}$. As can be known from $k=i_{max}/2$, $$k = \frac{1}{2}\left[\left[\frac{wd}{hz}\right] - 1\right]$$

and k is an integer when the two-dimensional ultrasonic image of the liver tissue is partitioned into rectangular regions of side length z, where $i_{max}$ is the maximum value in the value range of i.

The liver boundary region has a higher average gray value because the envelope region of liver is presented on a B-type ultrasonic image as uniform high-level echo. Additionally, the standard deviation of the grayscale is relatively low because the envelope region of liver appears uniform on the B-type ultrasonic image. In order to avoid the black background regions on two sides of the fan-shaped B-type ultrasonic image produced from the convex array probe scanning, the search will begin from the detection sub-region at the center line of the B-type ultrasonic image, and if the detection sub-region $R_{k1}$ is the one with the largest weight among a series of detection regions $R_{k1}$, the detection sub-region $R_{k1}$ is determined to be the liver tissue boundary.

The liver boundary identification method provided in the third embodiment is capable of realizing real-time automatic positioning of the liver tissue boundary via the B-type ultrasonic image of liver tissue. This algorithm has a low complexity level, which can offer higher efficiency when identifying the liver tissue boundary, thereby enabling real-time automatic positioning of the liver tissue boundary.

Fourth Embodiment

Figure 6:
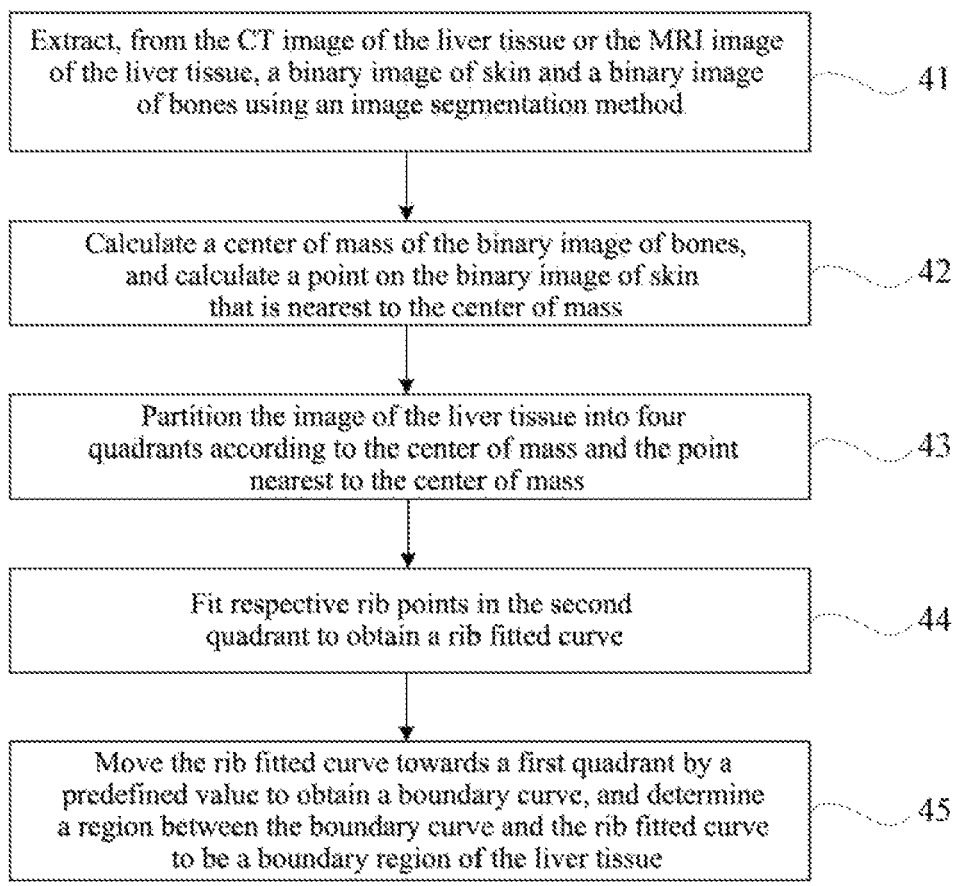
FIG. 6 is a flowchart implementing a liver boundary identification method provided in a fourth embodiment of the present disclosure.
Figure 7:
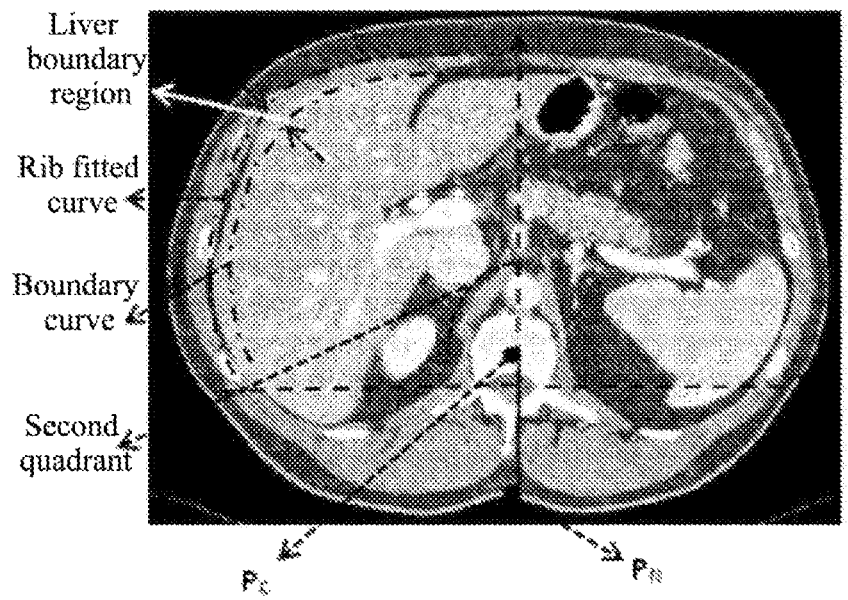
FIG. 7 is a schematic view illustrating an effect of boundary identification based on a CT image of a liver tissue in the fourth embodiment of the present disclosure.

The fourth embodiment is a particular optimization directed towards the Step 12 in the first embodiment of the present disclosure. The method is applicable to a three-dimensional ultrasonic signal of the liver tissue. FIG. 6 is a flowchart implementing a liver boundary identification method provided in a fourth embodiment of the present disclosure, and FIG. 7 is a schematic view illustrating an effect of boundary identification based on a CT image liver tissue in the fourth embodiment of the present disclosure. Combined with FIGS. 6 and 7, the method includes:

Step 41: extract, from the CT image of the liver tissue or the MRI image of the liver tissue, a binary image of skin and a binary image of bones using an image segmentation method.

The process begins from extracting a binary image of skin. The binary image of skin is extracted by using an image segmentation method (e.g. a region growing segmentation method) and taking the pixel of image coordinates (0, 0) as the seed point, where the region growing criterion corresponding to the CT value of air is [−1024, −500] HU (Hounsfield unit).

Then, the process proceeds to extracting a binary image of bones, including a binary image of the spine and a binary image of the rib. Threshold segmentation is performed for the whole image based on a threshold range of [350, 1024] HU to extract the binary image of bones.

Step 42: calculate a center of mass of the binary image of bones, and calculate a point on the binary image of skin that is nearest to the center of mass.

Calculate the center of mass $P_C$ of the binary image of bones. The center of mass of the spine $P_C$ is taken as the center of mass of the binary image of bones because the ribs are typically distributed symmetrically on the left and right hand side of the spine, and the spine takes up a relatively large proportion in the bone image.

Taking the center of mass $P_C$ of the spine as the starting point, search for the point on the binary image of skin that is nearest to the center of mass $P_C$ and denoted as $P_N$.

Step 43: partition the image of the liver tissue into four quadrants according to the center of mass and the point nearest to the center of mass.

In partitioning the image of the liver tissue into four quadrants by utilizing the center of mass $P_C$ and the point $P_N$ nearest to the center of mass, a straight line on which the center of mass $P_C$ and the point $P_N$ nearest to the center of mass are located is taken as the vertical axis, and a straight line passing through the center of mass $P_C$ and perpendicular to the vertical axis is taken as the horizontal axis. Most parts of the liver are located in the second quadrant.

Step 44: fit respective rib points in the second quadrant to obtain a rib fitted curve.

The rib fitted curve is obtained by fitting respective rib points in the second quadrant with a B spline or a skin curve.

Step 45: move the rib fitted curve towards a first quadrant by a predefined value to obtain a boundary curve, and determine a region between the boundary curve and the rib fitted curve to be a boundary region of the liver tissue.

Because the rib curve is close to the envelope of liver, the rib curve is moved inwards by a predefined value and then taken as the boundary curve, and the region between the boundary curve and the rib fitted curve is determined to be the boundary region of the liver tissue.

The predefined value may be 5 mm.

The liver boundary identification method provided in the fourth embodiment of the present disclosure is capable of realizing real-time automatic positioning of the liver tissue boundary via the CT image or MRI image of the liver tissue. Additionally, this algorithm has a low complexity level, which can offer higher efficiency in identifying the liver tissue boundary, thereby enabling real-time automatic positioning of the liver tissue boundary.

Fifth Embodiment

Figure 8:
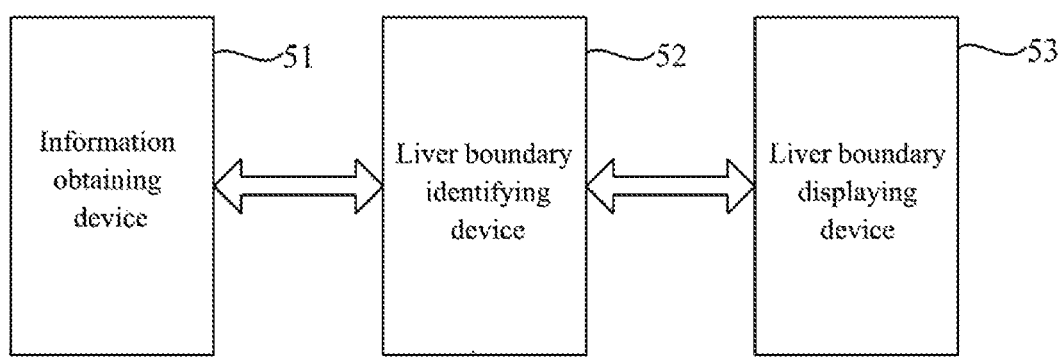
FIG. 8 is a schematic structural view illustrating a liver boundary identification system provided in a fifth embodiment of the present disclosure.

FIG. 8 is a schematic structural view illustrating a liver boundary identification system provided in a fifth embodiment of the present disclosure. As depicted in FIG. 8, a liver boundary identification system described in this embodiment may include an information obtaining device 51, a liver boundary identifying device 52, and a liver boundary displaying device 53, where the information obtaining device 51 is configured to obtain liver tissue information of a liver tissue to be identified; the liver boundary identifying device 52 is configured to identify a liver tissue boundary in the liver tissue information according to a feature of the liver tissue corresponding to the liver tissue information and a feature of the liver tissue boundary corresponding to the liver tissue information using an image processing technology or a signal processing technology; and the liver boundary displaying device 53 is configured to output position information of the identified liver tissue boundary.

If the liver tissue information is a one-dimensional ultrasonic signal of the liver tissue, a two-dimensional ultrasonic image of the liver tissue or a three-dimensional ultrasonic image of the liver tissue, the liver boundary identifying device 52 may include: a region partitioning unit, configured to partition the liver tissue information into a plurality of detection sub-regions; and a boundary determining unit, configured to: calculate a feature value of the liver tissue information in each of the detection sub-regions, and determine the liver tissue boundary according to the feature values of the liver tissue information in the detection sub-regions.

If the liver tissue information is a one-dimensional ultrasonic signal of the liver tissue, the boundary determining unit may include: a first feature value calculating sub-unit, configured to calculate a Nakagami distribution value $m_i$ for a one-dimensional ultrasonic signal $R_i$ of the liver tissue in each detection sub-region $S_i$; and a first boundary determining sub-unit, configured to: calculate a weight $W_i$ of each detection sub-region $S_i$ according to the following formula, and determine the detection sub-region corresponding to the maximum weight value to be a boundary region of the liver tissue:

$$W_i = \frac{100 * m_i}{\sqrt{d_i}}$$

where $d_i$ is scanning depth corresponding to the detection sub-region $S_i$.

If the liver tissue information is a two-dimensional ultrasonic image of the liver tissue, the region partitioning unit is specifically configured to partition the two-dimensional ultrasonic image of the liver tissue into a plurality of rectangular detection sub-regions $R_{ij}$; the boundary determining unit may be specifically configured to: calculate a weight $W_{kj}$ of each detection sub-region $R_{kj}$ according to the following formula, and determine the detection sub-region $R_{ij}$ corresponding to the maximum weight value to be a boundary region of the liver tissue:

$$W_{kj} = \frac{M_{kj}}{SD_{kj} * \sqrt{d_{kj}}}$$

where $M_{kj}$ is an average gray value of the two-dimensional ultrasonic image of the liver tissue in the detection sub-region $R_{kj}$, $SD_{kj}$ is standard deviation of grayscale of the two-dimensional ultrasonic image of the liver tissue in the detection sub-region $R_{kj}$, $d_{kj}$ is scanning depth corresponding to the detection sub-region $R_{kj}$, and $k=i_{max}/2$.

If the liver tissue information is a CT image of the liver tissue or an MRI image of the liver tissue, the liver boundary identifying device 52 may specifically include: a binary image obtaining unit, configured to extract, from the CT image of the liver tissue or the MRI image of the liver tissue, a binary image of skin and a binary image of bones using an image segmentation method; a feature point determining unit, configured to: calculate a center of mass of the binary image of bones; and calculate a point on the binary image of skin which is nearest to the center of mass; an image partitioning unit, configured to partition the image of the liver tissue into four quadrants according to the center of mass and the point nearest to the center of mass; a curve fitting unit, configured to fit each rib point in a second quadrant to obtain a rib fitted curve; and a boundary region determining unit, configured to: move the rib fitted curve towards a first quadrant by a predefined value to obtain a boundary region curve; and determine a region between the boundary region curve and the rib fitted curve to be a boundary region of the liver tissue.

According to the liver boundary identification system provided in the fifth embodiment of the present disclosure, the liver tissue boundary can be identified automatically and efficiently according to the feature of the liver tissue boundary corresponding to the liver tissue information, where the liver tissue information may be an A-type ultrasonic signal that reflects one-dimensional structural information of the liver tissue, or an M-type ultrasonic image or an M-type ultrasonic signal that reflects one-dimensional structural dynamic information of the tissue, or a B-type ultrasonic image that reflects a two-dimensional structure of the tissue, or a CT or MRI image that reflects a three-dimensional structure of the liver tissue.

The above described are merely preferred embodiments of, rather than limitations on, embodiments of the present disclosure. For those of ordinary skill in the art, various alterations and changes are possible for embodiments of the present disclosure. Any and all modifications, equivalent replacements, improvements and/or the like made within the spirit and principal of embodiments of the present disclosure should fall within the protection scope of embodiments of the present disclosure.

What is claimed is:

1. A liver boundary identification method, comprising:
obtaining liver tissue information of a liver tissue to be identified, wherein the liver tissue information is a one-dimensional ultrasonic signal of the liver tissue, a two-dimensional ultrasonic image of the liver tissue or a three-dimensional ultrasonic image of the liver tissue;
identifying a liver tissue boundary in the liver tissue information in real-time and automatically, according to a feature of the liver tissue corresponding to the liver tissue information and a feature of the liver tissue boundary corresponding to the liver tissue information using an image processing technology or a signal processing technology; and
outputting position information of the identified liver tissue boundary;
wherein the identifying a liver tissue boundary in the liver tissue information in real-time and automatically according to a feature of the liver tissue corresponding to the liver tissue information and a feature of the liver tissue boundary corresponding to the liver tissue information using an image processing technology or a signal processing technology comprises:
partitioning the liver tissue information into a plurality of detection sub-regions; and
calculating a feature value of the liver tissue information in each of the detection sub-regions, and determining at least one of the detection sub-regions to be the liver tissue boundary according to feature values of the liver tissue information in the detection sub-regions.

2. The method according to claim 1, wherein, the one-dimensional ultrasonic signal of the liver tissue comprises an A-type ultrasonic signal of the liver tissue or an M-type ultrasonic signal of the liver tissue, the two-dimensional ultrasonic image of the liver tissue comprises a B-type ultrasonic image of the liver tissue, the three-dimensional ultrasonic image of the liver tissue comprises a CT image of the liver tissue or an MRI image of the liver tissue.

3. The method according to claim 1, wherein, when the liver tissue information is the one-dimensional ultrasonic signal of the liver tissue, the calculating a feature value of the liver tissue information in each of the detection sub-regions, and determining at least one of the detection sub-regions to be the liver tissue boundary according to feature values of the liver tissue information in the detection sub-regions comprises:

calculating a Nakagami distribution value $m_i$ for a one-dimensional ultrasonic signal $R_i$ of the liver tissue in each detection sub-region $S_i$; and calculating a weight $W_i$ of each detection sub-region $S_i$ according to the following formula, and determining the detection sub-region corresponding to a maximum weight value to be a boundary region of the liver tissue:

$$W_i = \frac{100 * m_i}{\sqrt{d_i}}$$

where $d_i$ is scanning depth corresponding to the detection sub-region $S_i$, and i is a natural number.

4. The method according to claim 1, wherein, when the liver tissue information is the two-dimensional ultrasonic image of the liver tissue, the partitioning the liver tissue information into a plurality of detection sub-regions comprises: partitioning the two-dimensional ultrasonic image of the liver tissue into a plurality of rectangular detection sub-regions $R_{ij}$, i and j being natural numbers;

the calculating a feature value of the liver tissue information in each of the detection sub-regions, and determining at least one of the detection sub-regions to be the liver tissue boundary according to feature values of the liver tissue information in the detection sub-regions comprises:

calculating a weight $W_{kj}$ of each detection sub-region $R_{kj}$ according to the following formula, and determining the detection sub-region corresponding to a maximum weight value to be a boundary region of the liver tissue:

$$W_{kj} = \frac{M_{kj}}{SD_{kj} * \sqrt{d_{kj}}}$$

where $M_{kj}$ is an average gray value of the two-dimensional ultrasonic image of the liver tissue in the detection sub-region $R_{kj}$, $SD_{kj}$ is standard deviation of grayscale of the two-dimensional ultrasonic image of the liver tissue in the detection sub-region $R_{kj}$, $d_{kj}$ is scanning depth corresponding to the detection sub-region $R_{kj}$, $k=i_{max}/2$ and is a natural number, and $i_{max}$ is a maximum value in a value range of i.

5. The method according to claim 1, wherein outputting position information of the identified liver tissue boundary comprises:

outputting a coordinate position of the identified liver tissue boundary; and/or displaying an image of the identified liver tissue boundary.

6. The method according to claim 3, wherein outputting position information of the identified liver tissue boundary comprises:

outputting a coordinate position of the identified liver tissue boundary; and/or displaying an image of the identified liver tissue boundary.

7. The method according to claim 4, wherein outputting position information of the identified liver tissue boundary comprises:

outputting a coordinate position of the identified liver tissue boundary; and/or displaying an image of the identified liver tissue boundary.

8. A liver boundary identification system, comprising a processor and a memory having computer instructions stored therein, the processor, when executing the instructions, is configured to:

obtain liver tissue information of a liver tissue to be identified, wherein the liver tissue information is a one-dimensional ultrasonic signal of the liver tissue, a two-dimensional ultrasonic image of the liver tissue or a three-dimensional ultrasonic image of the liver tissue;

identify a liver tissue boundary in the liver tissue information in real-time and automatically, according to a feature of the liver tissue corresponding to the liver tissue information and a feature of the liver tissue boundary corresponding to the liver tissue information using an image processing technology or a signal processing technology; and output position information of the identified liver tissue boundary;

wherein the processor is further configured to:

partition the liver tissue information into a plurality of detection sub-regions; and calculate a feature value of the liver tissue information in each of the detection sub-regions, and determine at least one of the detection sub-regions to be the liver tissue boundary according to feature values of the liver tissue information in the detection sub-regions.

9. The system according to claim 8, wherein the one-dimensional ultrasonic signal of the liver tissue comprises an A-type ultrasonic signal of the liver tissue or an M-type ultrasonic signal of the liver tissue, the two-dimensional ultrasonic image of the liver tissue comprises a B-type ultrasonic image of the liver tissue, the three-dimensional ultrasonic image of the liver tissue comprises a CT image of the liver tissue or an MRI image of the liver tissue.

10. The system according to claim 8, wherein when the liver tissue information is the one-dimensional ultrasonic signal of the liver tissue, the processor is further configured to:

calculate a Nakagami distribution value $m_i$ for a one-dimensional ultrasonic signal $R_i$ of the liver tissue in each detection sub-region $S_i$; and calculate a weight $W_i$ of each detection sub-region $S_i$ according to the following formula, and determine the detection sub-region corresponding to a maximum weight value to be a boundary region of the liver tissue:

$$W_i = \frac{100 * m_i}{\sqrt{d_i}}$$

where $d_i$ is scanning depth corresponding to the detection sub-region $S_i$, and i is a natural number.

11. The system according to claim 8, wherein when the liver tissue information is the two-dimensional ultrasonic image of the liver tissue, the processor is further configured to:

partition the two-dimensional ultrasonic image of the liver tissue into a plurality of rectangular detection sub-regions $R_{ij}$, i and j being natural numbers; and calculate a weight $W_{kj}$ of each detection sub-region $R_{kj}$ according to the following formula, and determine the detection sub-region corresponding to a maximum weight value to be a boundary region of the liver tissue:

$$W_{kj} = \frac{M_{kj}}{SD_{kj} * \sqrt{d_{kj}}}$$

where $M_{kj}$ is an average gray value of the two-dimensional ultrasonic image of the liver tissue in the detection sub-region $R_{kj}$, $SD_{kj}$ is standard deviation of grayscale of the two-dimensional ultrasonic image of the liver tissue in the detection sub-region $R_{kj}$, $d_{kj}$ is scanning depth corresponding to the detection sub-region $R_{kj}$, $k=i_{max}/2$ and is a natural number, and $i_{max}$ is a maximum value in a value range of i.

12. The system according to claim 8, wherein when the liver tissue information is the CT image of the liver tissue or an MRI image of the liver tissue, the processor is further configured to:
    extract, from the CT image of the liver tissue or the MRI image of the liver tissue, a binary image of skin and a binary image of bones using an image segmentation method;
    calculate a center of mass of the binary image of bones; and calculate a point on the binary image of skin which is nearest to the center of mass;
    partition the CT image of the liver tissue or the MRI image of the liver tissue into four quadrants according to the center of mass and the point nearest to the center of mass;
    fit each rib point in a second quadrant to obtain a rib fitted curve; and
    move the rib fitted curve towards a first quadrant by a predefined value to obtain a boundary region curve; and determine a region between the boundary region curve and the rib fitted curve as a boundary region of the liver tissue.

13. The system according to claim 8, wherein the processor is further configured to:
    output a coordinate position of the identified liver tissue boundary; and/or
    display an image of the identified liver tissue boundary.

14. The system according to claim 9, wherein the processor is further configured to:
    output a coordinate position of the identified liver tissue boundary; and/or
    display an image of the identified liver tissue boundary.

15. The system according to claim 10, wherein the processor is further configured to:
    output a coordinate position of the identified liver tissue boundary; and/or
    display an image of the identified liver tissue boundary.

16. The system according to claim 11, wherein the processor is further configured to:
    output a coordinate position of the identified liver tissue boundary; and/or
    display an image of the identified liver tissue boundary.

17. The system according to claim 12, wherein the processor is further configured to:
    output a coordinate position of the identified liver tissue boundary; and/or
    display an image of the identified liver tissue boundary.

18. A liver boundary identification method, comprising:
    obtaining liver tissue information of a liver tissue to be identified, wherein the liver tissue information is a three-dimensional ultrasonic image of the liver tissue;
    identifying a liver tissue boundary in the liver tissue information in real-time and automatically, according to a feature of the liver tissue corresponding to the liver tissue information and a feature of the liver tissue boundary corresponding to the liver tissue information using an image processing technology or a signal processing technology; and
    outputting position information of the identified liver tissue boundary;
    wherein the liver tissue information is a CT image of the liver tissue or a MRI image of the liver tissue,
    the identifying a liver tissue boundary in the liver tissue information in real-time and automatically, according to a feature of the liver tissue corresponding to the liver tissue information and a feature of the liver tissue boundary corresponding to the liver tissue information using an image processing technology or a signal processing technology comprises:
    extracting, from the CT image of the liver tissue or the MRI image of the liver tissue, a binary image of skin and a binary image of bones using an image segmentation method;
    calculating a center of mass of the binary image of bones, and calculating a point on the binary image of skin which is nearest to the center of mass;
    partitioning the CT image of the liver tissue or the MRI image of the liver tissue into four quadrants according to the center of mass and the point nearest to the center of mass;
    fitting each rib point in a second quadrant to obtain a rib fitted curve; and
    moving the rib fitted curve towards a first quadrant by a predefined value to obtain a boundary curve, and determining a region between the boundary curve and the rib fitted curve to be a boundary region of the liver tissue.

19. The method according to claim 18, wherein outputting position information of the identified liver tissue boundary comprises:
    outputting a coordinate position of the identified liver tissue boundary; and/or
    displaying an image of the identified liver tissue boundary.

* * * * *